United States Patent [19]

Rosenberg et al.

[11] 4,419,351
[45] Dec. 6, 1983

[54] PLATINUM-DIOXOPYRIMIDINE COMPLEXES

[75] Inventors: Barnett Rosenberg, Holt; Loretta Van Camp, East Lansing; Robert G. Fischer, Lansing, all of Mich.; Samir Kansy, Eugene, Oreg.; Henry J. Peresie, Lafayette, Ind.; James P. Davidson, Lansing, Mich.

[73] Assignee: Research Corporation, New York, N.Y.

[21] Appl. No.: 970,524

[22] Filed: Dec. 18, 1978

Related U.S. Application Data

[63] Continuation of Ser. No. 803,269, Jun. 3, 1977, abandoned, which is a continuation of Ser. No. 508,854, Sep. 24, 1974, abandoned.

[51] Int. Cl.³ .............................................. A61K 31/505
[52] U.S. Cl. .................................. 424/245; 424/180; 536/23; 536/29; 544/225
[58] Field of Search ..................... 544/225; 424/245; 536/23

[56] References Cited

PUBLICATIONS

Cleare et al., Coordination Chemistry Reviews, vol. 12, pp. 349 and 399–405, Jun. 1974.
Rosenberg, Die Naturwissenschaften, vol. 69, pp. 399–406 (1973).
Connors et al., Platinum Coordin. Complexes in Cancer Chemother., title pp. IX, 40–41, 51, 61 and 66 (1974).
Gelfman et al., Russian J. of Inorganic Chemistry, vol. 5, pp. 16-2-1604 (1970).
Mansy et al., J. Am. Chem. Soc. vol. 95, pp. 1633–1646 (1973).

Primary Examiner—Jane T. Fan
Attorney, Agent, or Firm—Dennis P. Clarke

[57] ABSTRACT

A platinum-[2,4-dioxopyrimidine] complex and pharmaceutical composition suitable as an anti-tumor, anti-bacterial and anti-viral agent and process for the manufacture thereof comprising reacting a 2,4-dioxopyrimidine having the formula

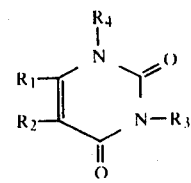

wherein $R_1$, $R_2$, $R_3$ and $R_4$ are suitable substituents with cis-diaquodiamineplatinum (II).

8 Claims, 1 Drawing Figure

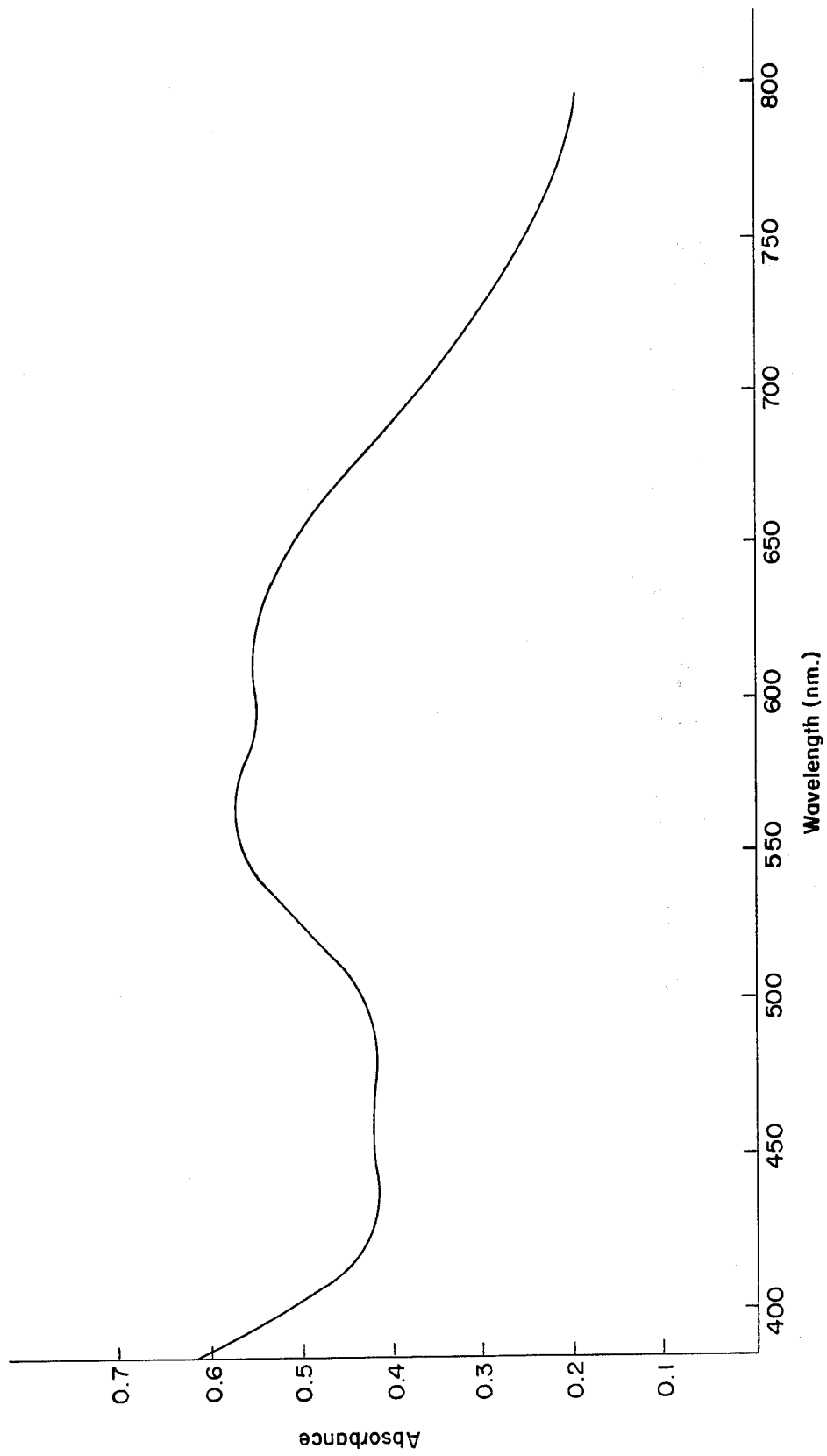

PLATINUM-DIOXOPYRIMIDINE COMPLEXES

The invention described herein was made in the course of work under a grant or award from the Department of Health and Human Services.

This is a continuation, of application Ser. No. 803,269, filed June 3, 1977, now abandoned which is a continuation of Ser. No. 508,854, filed Sept. 24, 1974 abandoned.

BACKGROUND OF THE INVENTION

Various platinum coordination compounds useful as anti-tumor agents are disclosed in co-pending application Ser. No. 405,184, filed Oct. 10, 1973 (which is a continuation application of application Ser. No. 230,533, filed Feb. 29, 1972, which is a continuation application of application Ser. No. 30,239, filed Apr. 20, 1970). Another class of platinum coordination compounds, i.e., malanato-platinum compounds, useful as anti-tumor agents are disclosed in co-pending application Ser. No. 260,989 (filed June 8, 1972). A method for the treatment of viral conditions utilizing platinum coordination compounds is disclosed in co-pending application Ser. No. 350,924, filed Apr. 13, 1973.

While extremely effective against a variety of tumors, the above-described platinum coordination compounds suffer from the disadvantages of (1) having a high level of renal toxicity, and (2) a low solubility in water. The latter characteristic renders the preparation of therapeutically useful compositions difficult.

It has been discovered that a certain class of platinum "blue" complexes have a high anti-tumor activity, are soluble in water, and have a low level of renal toxicity.

The prior art has long been aware of the so-called "platinblau" complexes. Credit for the discovery of "Platinblau", as these blue complexes were designated, is usually given to Hofmann and Bugge (Ber. 41: 312–314, 1908). They reacted $Ag_2SO_4$ with the yellow platinum (II) coordination compound, $Pt(CH_3CN)_2Cl_2$ in aqueous solution and isolated a deep blue, amorphous material. It was thought to be monomeric in nature, containing platinum in the divalent state. Since this discovery only a few papers have appeared concerning further studies on "Platinblau" and similar blue products. Gillard and Wilkinson (J. Chem. Soc., 2835–37, 1964) postulated that "Platinblau" had the empirical formula $Pt(CH_3CONH)_2.H_2O$ with polymeric chains, bridging acetamide groups, and divalent platinum. Brown et al. (J.A.C.S. 91:11: 2895–2902, 1969 and 90:20: 5621–5622, 1968) have attempted to demonstrate that it is a platinum (IV) complex containing chelating acetamide ligands, and hydroxyl groups in the other two coordination positions. We have found that both blue and purple products could be isolated from the "Platinblau" reaction, with the purple species being the more highly oxidized (vide infra). Thus, there is considerable controversy over the exact nature of this complex. Brown et al (ibid.) have also reported the preparation of highly colored amide complexes of platinum by heating, for example, trimethylacetamide and either $Pt(CH_3CN)_2Cl_2$ or $K_2[PtCl_4]$ (a reddish colored salt). From this reaction three components were identified by chromatography. These were two yellow crystalline materials and a blue amorphous powder. Although they reported that they could not identify any of these blue products in a positive manner, they postulated that the blue material contained tetravalent platinum, which bidentate anide anions and chloride ligands completing the coordination sphere.

The only other reference to anomalously colored platinum compounds containing cis-amino groups as ligands rather than amides is that concerning mixture of cis-dichlorodiammineplatinum (II) and sulfuric acid (Gillard et al, ibid.). Crystals of this blue black material were obtained and a preliminary X-ray diffraction study showed that the Pt-Pt distance was 3.06 Å, suggesting strong interaction. They concluded that this complex contained layers of cis-dichlorodiammineplatinum (II) held together by Pt-Pt bonds, with the sulfate ion hydrogen bonded to the coordinated ammonia groups.

SUMMARY OF THE INVENTION

The invention is predicated on the discovery that the "platinum blue" complexes formed by the reaction of cis-diaquodiammineplatinum II with a 2,4-dioxopyrimidine are anti-tumor, anti-viral and anti-bacterial agents with a low level of renal toxicity and a high degree of solubility in water.

Suitable 2,4-dioxopyrimidines include those having the formula:

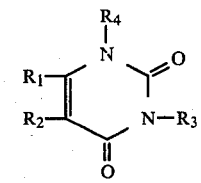

wherein:

$R_1$ and $R_2$ may be the same or different and are selected from the group consisting of H, lower alkyl, dilower alkyl amino, di-halo lower alkyl amino, halogen, hydroxy, hydroxy lower alkyl, carboloweralkoxy, $R_3$ and $R_4$ may be the same or different and are selected from the group consisting of H, lower alkyl ribosyl, deoxyribosyl, triacetyl, tribenzoyl or 2',3'-loweralkylidine ribosyl, ribosyl, ribosyl phosphates or deoxyribosyl phosphates, or the 5,6-2H derivatives thereof.

The invention also relates to a method for preparing the platinum-[2,4-dioxopyrimidine] complexes by reacting the above-described 2,4-dioxopyrimidines with cis-diaquodiammineplatinum (II) wherein the molar ratio of pyrimidine to platinum compound is from about 2:1 to about 1:1 at a temperature of from about 0° to about 55° C., and for a time sufficient to form the complex.

The invention also relates to a pharmaceutical composition adapted for the treatment of tumors, bacterial and viral infections and arthritic conditions comprising, in dosage unit form, a pharmaceutically acceptable carrier and from about 1 mg/ml to about 50 mg/ml of a complex of 2,4-dioxopyrimidine and platinum compound as described above.

The present invention also relates to a method for the treatment of tumors and bacterial and viral infections comprising the administration to a living being afflicted with the malady from about 1 mg/kg to about 800 mg/kg of body weight of the above-described complex.

DETAILED DESCRIPTION OF THE INVENTION

Although the complexes of the invention are referred to as "platinum blue" complexes for purposes of convenience, the products of some of the above-described reactions are in reality mixtures which are extremely difficult to separate. Analysis and molecular weight determinations have enabled certain conclusions to be drawn.

Generally, the complexes contain one pyrimidine molecule per molecule of platinum. For the most part, each complex contains two ammonia ligands, one pyrimidine anion and one hydroxide ion per platinum molecule, but with two additional oxygen atoms at an unspecifiable location. The 5-fluorouracil complex is an exception in that it does not contain excess oxygen.

The cis-diammino configuration of platinum appears to be essential for forming the complexes of the invention.

Although the 2,4-dioxopyrimidine moiety of the platinum complex may be variously substituted in the 1,3,5, and 6 positions as set forth above, the preferred complexes are those wherein $R_1$, $R_2$, $R_3$ and $R_4$ are each hydrogen and wherein $R_1$, $R_2$ and $R_3$ are each hydrogen and $R_2$ is $CH_3$. These compounds are uracil and thymine. The complexes formed by the reaction of uracil and thymine with cis-diaquodiammmineplatinum (II) have been found to be especially effective anti-tumor, anti-bacterial and anti-viral agents.

As noted above, the exact structure of these complexes is at present unknown. They are, however, extremely soluble in water. They may be prepared by reacting the appropriate 2,4-dioxopyrimidine with cis-diaquodiammineplatinum (II) in an aqueous solution wherein the molar ratio of 2,4-dioxopyrimidine to the platinum complex is from about 2:1 to about 1: at a temperature in the range of from about 0° to about 55° C., preferably at room temperature, for a time sufficient for the complex to form, preferably from about 1 to about 21 days. The method is preferably carried out in an aqueous medium wherein the pH ranges from about 3 to about 8, preferably about 6.5.

The most notable characteristic of the compounds of the invention is their extreme solubility in water, i.e., on the order of 1 g per 10 ml of water. Their extreme solubility renders them particularly adapted for the treatment of tumors and bacterial and viral infections in living beings.

For example, the cis-diaquodiammineplatinum(II)-uracil complex was found to be particularly effective against the ascites Sarcoma-180 tumor in the Swiss white mouse. The toxicity of the complex was extremely low and the mice tolerated up to 500 mg per kg of body weight as a single dose injection of the complex without any deaths.

The complex described above was also found to be effective against the Fowl Pox virus when incubated therewith for extremely short periods of time prior to innoculation into an embryonated egg as a system. It was also found that the complex could be injected into the egg well after the innoculation with the virus and still prevent development of the pox formation typical of a live virus attack upon the membrane.

As another example of the diversified activity of the platinum-uracil complex, it was tested against E. coli growing in test tube cultures. Even at very low concentrations, i.e., 5 ppm, tha bacteria formed clumps and did not show filamentation. At higher concentrations, i.e., greater than 40 ppm, the bacteria were completely killed.

The platinum-uracil complex has also been found to be effective against the ADJ/PC6 tumor system.

The complexes of the invention may be compounded with conventional pharmaceutical carriers in the preparation of pharmaceutical compositions for the treatment of tumors, bacterial and viral infections. The compositions should comprise, in dosage unit form, a pharmaceutically acceptable carrier and from about 0.1 mg/ml to about 50 mg/ml of the above-described complex.

The mode of administration of the platinum-uracil and related complexes will depend upon the particular malady to be treated. Solutions may be administered by injection via the intraperitoneal, intramuscular, subcutaneous or intravenal routes, or as a solid, per oz.

The invention is illustrated by the following non-limiting Examples:

EXAMPLE 1

3 grams of cis-dichlorodiammineplatinum (II) (0.01 moles) and 0.02 moles of silver nitrate in 100 ml of water were stirred overnight at 23° C. in the dark. The silver removes the chlorides from the platinum complex and produces 100% yields of the cis-diaquodiammineplatinum (II). The silver chloride is then filtered off. It is necessary to remove all of the silver ions from solution. A small aliquot of the remaining solution is tested for excess silver by adding a small amount of 0.1 molar HCl. If the solution turns cloudy the reaction has not yet proceeded to completion. When the solution remains clear, the reaction is considered complete. The solution is then neutralized with 2.0 normal sodium hydroxide to yield a final pH value of between 6 and 7. Then, 1.12 grams of uracil is dissolved in 100 milliliters of water to form a slurry. The pH is then adjusted to 9 with 2.0 normal sodium hydroxide and warmed to 50° C. to dissolve the uracil to give a solution containing 0.01 moles of uracil. The uracil solution is then mixed with the cis-diaquodiammineplatinum(II) complex to provide a 1 to 1 ratio on a molecular basis of the two reactants. The pH is adjusted to between 6 and 7. The vessel is stoppered, covered with aluminum foil, and placed in a water bath at 37° C. for a period of one week to complete the reaction. A blue color forms after approximately 24 hours. After one week there is a small amount of blue precipitate. The solution is cooled to near 0° overnight and a large amount of a blue precipitate forms. This is filtered, and washed with a very small amount of cold water. The filtrate is washed three times with large amounts (approximately 150 milliliters each time) of 200 proof, boiling ethanol to remove excess uracil that may be present. After the third wash the ethanol when cooled should remain clear, indicating no further free uracil in solution. The filtrate is air dried, then vacuum dried for 12 hours at 40° C. The result is a dark blue, powdery, pure sample of the Platinum-Uracil complex.

The supernatent liquid from the initial filtration was evaporated to about 25% of its original volume and an equal volume of ethanol was added. Cooling to 0° C. gave more blue precipitate and a dark-green solution. The blue precipitate was filtered and the filtrate further concentrated. The addition of more ethanol gave a pale-green precipitate.

Obviously, therefore, the method of the invention yields a complex mixture of "platinum blue" compounds. It is to be understood, however, that the invention includes all of the diverse components of the reaction mixture, whether in admixture or in isolated form.

Generally, the first derived precipitate, i.e., the blue precipitates are less soluble in water-ethanol mixtures.

The second derived component is more soluble in water-ethanol.

EXAMPLE 2

The procedure of Example 1 was followed utilizing 2′,3′,5′-triacetyluridine except that the solution was evaporated to dryness and the complex dissolved in ethanol. Addition of ether gave a dark-blue hygroscopic precipitate which was collected and washed with ether.

EXAMPLES 3–13

The procedure of Example 1 was followed in preparing the complexes set forth in Table 1. The Elemental Analyses of the complexes of Examples 1 and 3–14 are also set forth in Table 1.

TABLE 1

| Compound | Elemental Analyses of Complexes | | | | | | | |
|---|---|---|---|---|---|---|---|---|
| | % C | % H | % N | % O | % Cl | % F | % Pt | M W |
| CLASS IA ("blue" or 1st precipitate) | | | | | | | | |
| uracil (Ex. 1) | 12.31 | 2.49 | 14.55 | 20.65 | — | — | 50.00* | 805 |
| thymine (Ex. 3) | 14.05 | 3.26 | 15.65 | 18.97 | — | — | 48.07* | — |
| 5,6-dihydro-6-methyluracil (Ex. 4) | 13.07 | 3.36 | 15.60 | 17.21 | — | — | 50.76* | — |
| 5,6-dihydrothymine (Ex. 5) | 11.65 | 2.69 | 13.29 | 10.55 | — | — | 61.82* | 283 |
| 1-methyluracil (Ex. 6) | 14.65 | 2.63 | 14.08 | 19.77 | — | — | 48.87* | — |
| 5,6-dimethyluracil (Ex. 7) | 16.96 | 3.38 | 15.07 | 15.78 | — | — | 48.81* | — |
| 5-carbethoxyuracil (Ex. 8) | 17.94 | 3.07 | 13.91 | 15.86 | — | — | 49.22* | — |
| 5-chlorouracil (Ex. 9) | 10.16 | 2.17 | 14.91 | 17.98 | 8.76 | — | 46.02* | — |
| 6-chlorouracil (Ex. 10) | 11.24 | 2.45 | 13.37 | 18.63 | 8.28 | — | 46.03* | 433 |
| 5-hydroxymethyluracil (Ex. 11) | 12.25 | 1.68 | 14.47 | 20.48 | — | — | 50.12* | 379 |
| CLASS IB ("green" or 2nd precipitate) | | | | | | | | |
| uracil (Ex. 1) | 11.68 | 2.59 | 14.23 | 23.95 | — | — | 47.55* | — |
| thymine (Ex. 3) | 14.55 | 3.20 | 15.45 | 19.63 | — | — | 47.17* | 388 |
| 1-methylthymine (Ex. 12) | 16.17 | 3.05 | 15.53 | 17.81 | — | — | 47.44* | 371 |
| CLASS IA ("blue") | | | | | | | | |
| 5-fluorouracil (Ex. 13) | | | | | | | | |
| calc. for PtC$_4$H$_9$N$_4$O$_3$F | 12.80 | 2.42 | 14.93 | — | — | 5.06 | — | 375 |
| found | 12.65 | 2.26 | 14.75 | — | — | 509 | — | 381 |
| CLASS IB ("green") | | | | | | | | |
| 5-fluorouracil (Ex. 13) | | | | | | | | |
| calc. for PtC$_4$H$_9$N$_4$O$_3$F | 12.80 | 2.42 | 14.93 | — | — | 5.06 | — | 375 |
| found | 13.05 | 2.36 | 15.09 | — | — | 5.17 | — | 374 |

*calculated by difference

Some of the "platinum blue" complexes of the invention are believed to be mixtures of oligomeric species including monomers, dimers and trimers.

It is, for this reason, difficult to interpret the infrared spectra of the complexes with regard to structural features. They are characterized by the fact that they have an absorption band in the visible red region, consisting either of a single or a double peak which imparts the characteristic green, blue or violet color to the various complexes. An absorption spectrum of the cis-diaquodiammineplatinum (II)-uracil complex as prepared above is shown in FIG. I. It can be assumed from the infrared spectra that the ammine ligands are present and that a ring structure still exists. While possessing high solubilities in water, the complexes have very limited solubilities in solvents such as dimethylformamide and dimethylsulfoxide.

X-ray diffraction and electron diffraction analyses of the platinum-uracil complex show a completely amorphous material.

Conductivity tests suggest that the complexes are neutral species.

The visible spectra of a number of different samples of the platinum-uracil complexes were measured on a Cary 15 Spectrophotometer in aqueous solution in 1 cm quartz cells at concentrations of 10 mg/10 ml (1 mg/ml). For a sample which analyzed to have a M.W.=1200 the spectrum contained a broad band centered at 722 nm with absorbance ≅0.9 and a broad shoulder at 582 nm (O.D.=0.74). A sample believed to be a monomeric species (m.w.≅400) had a broad shoulder at 617 nm (O.D.=0.6), a broad band at 563 nm (O.D.=0.62) and a band at 468 nm (O.D.=0.42).

The proton magnetic resonance spectra of the platinum-uracil, thymine and 5,6-dimethyluracil complexes samples were recorded in a Varian A56/60 Spectrometer in $D_2O$ solution using DSS (a water soluble form of TMS) as internal reference (set to 0 ppm). The platinum-uracil complex exhibited a sharp doublet centered at 2.84 ppm (peaks at 2.76 and 2.92 ppm), a peak due to the solvent at 4.47 ppm and a weak broad (1 ppm width at half height) at 7.69 ppm. For the Pt-Thymine complex, with the solvent peak adjusted to 4.47 ppm, the spectrum showed a broad (2 ppm width at half height) peak at 1.71 ppm, a sharp doublet centered at 2.85 ppm (peaks at 2.77 and 2.93 ppm) and a weak broad peak (1 ppm wide) at 7.5 ppm (possibly due to unreacted free base). Free uridine in $D_2O$ gives pmr spectrum with a doublet assigned to the uracil $H_6$ protons at 7.65 ppm and a doublet due to the $H_5$ protons at 5.8) ppm (solvent peak 4.54 and DDS at 0 ppm). Free thymine in $d_7$-DMF solutions has a sharp peak at 1.72 ppm assigned to methyl protons and a broad weak peak at 7.20 ppm (assigned to $H_6$) with TMS set at 0 ppm. The spectrum of the 5,6-dimethyluracil compound contained peaks at 1.76 and 2.07 ppm relative to HDO at 4.47 ppm. From these spectra we can only conclude that the magnetic environment of the protons in the bases changes when they become coordinated in these blue complexes to increase the shielding of the protons.

The electron scattering for chemical analysis (ESCA) measurements on the binding energy of the 4f electrons in a platinum from X-ray Photoelectron Spectroscopy yields a value for cis-Pt(NH$_3$)$_2$CL$_2$ of 73.02 Ev. The platinum in the platinum-uracil complex gave a value of 73.6 eV. This suggests that the valence state of platinum in the platinum-uracil is II and not IV.

The electronic absorption spectra of the blue precipitate of the platinum-uracil complex contain broad absorption bands in the vicinity of 550-650 nm with molar extinction coefficients on the order of 500-1000 1 mole$^{-1}$ cm$^{-1}$. The green precipitate fraction of the platinum uracil complex contains a single broad band near 720 nm of similar intensity. These blue and green compounds contain a very intense band near 290 nm.

The chemotherapeutic activities of the "Platinum Blue" complexes were determined using the ascites Sarcoma-180 tumor in Swiss White mice. The protocols for these tests were as follows: Random bred female Swiss White mice (Spartan Laboratory, Williamston, Mich.) of 18-20 grams weight were randomized in groups of six. The ascites cells were removed from the peritoneal cavities of animals with approximately 10 day old ascites tumors. The cells were washed several times with 0.85% saline and spun down each time in a refrigerated centrifuge for 3-5 minutes at 750 r.p.m. After the blood was removed from the cells, they were diluted with 0.85% saline solution and counted in a hemocytometer. A final dilution of $2 \times 10^7$ cells/ml. in saline was made. Each animal received 0.2 ml. of this suspension ($4 \times 10^6$ cells/animals). This was injected intraperitoneally on day 0 of each test. Two groups (12 animals) were kept as negative controls, and the test was terminated at twice the mean day of death of the negative controls. Two groups (12 animals) were the positive controls which were injected i.p. on day 1 with solution of cis-dichlorodiammineplatinum(II) in saline at a dose of 7 mg/kg. All test compounds were injected i.p. on day one as a 0.5 ml. volume of the compound in a carrier of water, physiologic saline or arachis oil (peanut oil). Soluble compounds were always tested in appropriate solutions, the insoluble ones as a slurry. The slurry was sonicated for periods of up to 10 minutes to insure uniformity of dispersion just prior to injections. Generally, four dose levels, in a doubling escalation, were tested for each compound. Retests were performed if a sufficient level of drug toxicity at the highest dose was not reached. Animals still alive at the completion of the tests were considered to have died on the day of evaluation. Animals showing no abdominal distention (by palpation, or visibly) on this day were considered cured. Some cured animals later developed a solid tumor around the site of injection of the cells. This is believed to be due to a leakage of cells along the route of the needle on injection, or a later leak of cells through the injection hole in the peritoneum. In any case, this is considered an adventitious effect, which, when care is used in injections and smaller needles are used, becomes negligible.

The compounds tested were usually freshly prepared and purified. The compounds kept for further testing were stored in a vacuum dessicator in a dark refrigerator to prevent deterioration. In general, compounds of all classes tested had toxic levels at 200 mg/kg or greater. Toxic levels are considered to be that concentration where 2 or more of the 6 animals at the dose died within 8 days of injection. Animals dying after this time overlap with the early deaths of the negative controls.

For some of the complexes tested, the animals exhibited an excessive extension of the hind legs shortly after injection at high dose levels. The animals surviving the first two days, however, usually survived past the eight-day limit for toxic deaths. Some, however, did show an early death. Consistent with early experience with platinum complexes, gross hepatic damage was minimal or non-existent (with the exceptions of Pt(CH$_3$CN)$_2$Cl$_2$, the platinum-1-methyluracil and the platinum-5-bromo-1-methyluracil complexes. Peritonitis occurred in a similar number of cases at later times (day of evaluation, and up to 3 months later in cured animals). Symptoms of neuromuscular disorders were observed with a few compounds, shortly after high dose injections (i.e. platinum-uracil green precipitate). No symptoms of central nervous system disorders were ever observed in the test animals.

Unlike the solid Sarcoma-180, the ascites tumor in the Swiss White mice elicits no spontaneous regression (0/336), all tumored mice die, and the percent of no-takes is zero. The mean day of death is 17.5, with a small standard deviation ($\pm 2.2$ days).

The results of the survey tests are presented in Table 2. The letter A indicates the "blue" or first isolated precipitate, the letter B, the "green" or second precipitate. The data shown includes the carrier; the dose range tested; the toxic level (see above); the best percent increase in lifespan (% ILS), the maximum being 100% since the experiments were terminated at twice the mean life span of the negative controls; the dose level giving the best % ILS; the physical state of the inoculum (solution or slurry); and finally, the number of cured animals (out of 6 in each group).

TABLE 2

Survey Results of Antitumor Activity of Platinum Blue Complexes Against the Ascites Sarcoma 180 Tumor in Swiss White Mice

| Compound | Carrier[b] | Range | Toxic Level | Best % ILS | Dose of Best % ILS | Physical State[c] | # of cures[d] |
|---|---|---|---|---|---|---|---|
| negative control - average day of death = 17.5 (S.D. $\pm$ 2.16) | | | | | | | |
| positive control cis-Pt(II)(NH$_3$)$_2$Cl$_2$ | S | 7 | 10 | 49 (S.D $\pm$ 2.82) | 7 | S | 1 (of 12) |
| CLASS IA[a] | | | | | | | |
| uracil | W | 50-400 | 400 | 92 | 200 | S | 5 |
| uracil | S | 50-400 | 400 | 80 | 100 | S | 1 |
| 5,6-dihydrouracil | W | 20-800 | 400 | 92 | 200 | S | 4 |
| thymine | W | 150-600 | 450 | 72 | 300 | S | 2 |
| thymine | S | 50-200 | >200 | 67 | 150 | S | 1 |
| 5,6-dihydro-6-methyl uracil | W | 50-400 | 200 | 89 | 50 | S | 2 |
| 6-methyluracil | S | 200-800 | >800 | 87 | 600 | S | 3 |
| 5,6-dimethyluracil | W | 50-400 | >400 | 100 | 400 | S | 5 |
| 5,6-dihydrothymine | S | 50-400 | 400 | 87 | 200 | S | 2 |
| 1-methyluracil | S | 50-400 | >400 | 85 | 400 | S | 3 |
| 1-methylthymine | S | 50-400 | 400 | 94 | 100 | S | 3 |
| 1-ethyluracil | S | 50-400 | 200 | 38 | 50 | S | 0 |
| 5-fluorouracil | W | 50-400 | 200 | 90 | 100 | S | 4 |
| 5-chlorouracil | W | 50-400 | 200 | 67 | 50 | S | 3 |
| 6-chlorouracil | S | 25-200 | >200 | 88 | 200 | S | 3 |

TABLE 2-continued

Survey Results of Antitumor Activity of Platinum Blue Complexes Against the Ascites Sarcoma 180 Tumor in Swiss White Mice

| Compound | Carrier[b] | Range | Toxic Level | Best % ILS | Dose of Best % ILS | Physical State[c] | # of cures[d] |
|---|---|---|---|---|---|---|---|
| 5-bromo-methyl-uracil | S | 50–400 | >400 | 88 | 200 | S | 1 |
| 5-iodouracil | P.O. | 25–600 | 500 | 8 | 250 | Sl | 0 |
| 5-hydroxymethyluracil | S | 50–400 | 200 | 98 | 100 | S | 2 |
| 5-carbethoxyuracil | S | 25–200 | 200 | 56 | 200 | S | 0 |
| 6-carbomethoxyuracil | S | 25–200 | >200 | 38 | 25 | S | 0 |
| uridine deoxyribose | S | 25–200 | >200 | 46 | 200 | S | 0 |
| thymidine | S | 50–400 | 200 | 46 | 50 | S | 1 |
| 5-iodouridine deoxyribose | P.O. | 50–200 | >200 | 23 | 200 | Sl | 0 |
| 2′,3′,5′-triacetyl-uridine | S | 50–1000 | 800 | 79 | 600 | S | 2 |
| 2′,3′,5′-tribenzoyl-uridine | S | 50–400 | >400 | 19 | 100 & 200 | S | 0 |
| 2′,3′-isopropylidine-uridine | S | 50–400 | 400 | 61 | 50 | S | 2 |
| CLASS IB | | | | | | | |
| uracil | W | 25–675 | 500 | 95 | 340 | S | 4 |
| thymine | S | 50–400 | >400 | 60 | 200 | S | 0 |
| 1-methylthymine (yellow) | S | 50–400 | 400 | −14 | 100 | S | 0 |
| 1-ethyluracil | S | 50–400 | 100 | 15 | 50 | Sl | 0 |
| 5-fluorouracil | S | 25–200 | >200 | 37 | 200 | S | 0 |
| MISC. | | | | | | | |
| Pt(CH$_3$CN)$_2$Cl$_2$* | S | 6.3–50 | 50 | 83 | 25 | S | 1 |

*Prepared by hydrolysis of Pt(CH$_3$CN)$_2$Cl$_2$
[a]Refer to section IV for a description of the Class
[b]W = water, S = saline, P.O. = peanut oil
[c]S = solution, Sl = slurry
[d]6 animals per test, cures are considered as having no distention of abdominal cavity but do include formation of solid tumors at site of injection in some cases.

The results in Table 2 were obtained using a single i.p. injection on day 1. Since this may not be the best schedule for treatment, samples of the drugs were selected for schedule dependency tests. These are described in Table 3. The cis-dichlorodiammineplatinum(II) given as 8 injections of 1 mg/kg each every 3 hours for the first day showed a surprisingly improved result over the single injection of 7 mg/kg (positive control).

TABLE 3

Results of Schedule Dependency Tests of Antitumor Activity of Selected Platinum Blue Complexes

| Compound[a] | Frequency of Injections | Number of Injections | Carrier[b] | Range | Toxic Level | Best % ILS | Dose of Best % ILS | Physical[c] State | # of cures[d] |
|---|---|---|---|---|---|---|---|---|---|
| Negative Control - Average Day of Death 19.3 (S.D. ± 3.2) | | | | | | | | | |
| Positive Control cis-Pt(II)(NH$_3$)$_2$Cl$_2$ | day 1 | 1 | S | 7 | 10 | 42 (S.D. ± 3.1) | 7 | S | 1 |
| cis-Pt(II)(NH$_3$)$_2$Cl$_2$ | every 3 hrs. | 8 | S | 1 | >1 | 86 | 1 | S | 5 |
| | every day | 5 | S | 3 | 3 | 19* | 3 | S | 3 |
| | every 5th day | 5 | S | 45 | >5 | 83 | 5 | S | 3 |
| Uracil Class IA | every 3 hrs. | 8 | S | 50–125 | 100 | 80 | 50 | S | 1 |
| | every day | 5 | S | 50–150 | >150 | 100 | 100 | S | 6 |
| | every 5th day | 5 | S | 75–300 | >300 | 100 | 150 | S | 3 |
| Uracil Class IB | every 3 hrs. | 4 | S | 100–250 | >250** | 73 | 100 | S | 3 |
| | every day | 5 | S | 25–200 | 200 | 68 | 100 | S | 5 |
| | every 5th day | 5 | S | 100–400 | 400 | 84 | 200 | S | 5 |
| Thymine Class IA | every 3 hrs. | 8 | S | 50–200 | 200** | 77 | 100 | S | 4 |
| | every day | 5 | S | 50–150 | 150** | 91 | 50 | S | 5 |
| | every 5th day | 5 | S | 75–300 | 300 | 100 | 150 | S | 5 |

*Three animals died within 9 days of start - remainder cured.
**Number of injections varied because of severe animal response. Therefore, toxicity probably would have been reached had all animals received the same number of injections.
[a]Refer to section 4 for a description of the classes.
[b]S = saline
[c]S = solution, Sl = slurry
[d]6 animals per test, cures are considered as having no distention of abdominal cavity but do include formation of solid tumors at site of injection in some cases.

Tables 4–7, respectively, tabulate the results achieved when employing the complexes of the invention against the L1210, MCDV 12, (Rauscher Leukemia, virus-induced), Ehrlich Ascites and the ADJ PC6A (myeloma) tumors.

TABLE 4

Effects of 'Platinum Blue' Complexes on the L1210 Tumor in BDF Mice[a]

| Compound | Dose and Schedule | % ILS | Survivors |
|---|---|---|---|
| uracil Class IA | 50 mg/kg qid × 5 | 16 | 0/3 |
| | 100 mg/kg qid × 5 | 26 | 0/3 |
| | 61.25 mg/kg q3 hr × 8 | 30 | 0/3 |
| | 30.63 mg/kg q3 hr × 8 | 0 | 0/3 |
| | 250 mg/kg × 1 | 27 | 0/3 |
| | 500 mg/kg × 1 | −58 | 0/3 |
| thymine Class IA | 100 mg/kg qid × 5 | 25 | 0/3 |
| | 30.63 mg/kg q3 hr × 8 | 32 | 0/3 |
| | 61.25 mg/kg q3 hr × 8 | 32 | 0/3 |

TABLE 4-continued

Effects of 'Platinum Blue' Complexes on the L1210 Tumor in BDF Mice[a]

| Compound | Dose and Schedule | | % ILS | Survivors |
|---|---|---|---|---|
| 5,6-dihydrothymine | 50 | mg/kg qid × 5 | 36 | 0/3 |
| Class IA | 100 | mg/kg qid × 5 | 45 | 0/3 |
| | 30.63 | mg/kg q3 hr × 8 | 30 | 0/3 |
| | 61.25 | mg/kg q3 hr × 8 | 0 | 0/3 |
| 1-methyluracil | 50 | mg/kg qid × 5 | 10 | 0/3 |
| Class IA | 100 | mg/kg qid × 5 | 28 | 0/3 |
| | 30.63 | mg/kg q3 hr × 8 | 10 | 0/3 |
| | 61.25 | mg/kg q3 hr × 8 | 22 | 0/3 |

[a]All experiments were terminated arbitrarily at 200% ILS and any survivors were tabulated at that time. All therapy was started on the third day after tumor transplant. Untreated tumor controls died 10-11 days after transplant. In some instances efforts to reproduce above results have shown considerable variability.

TABLE 5

Effects of cis-Dichlorodiammineplatinum (II) and 'Platinum Blues' on MCDV 12 (Rauscher Leukemia, Virus Induced) in BALB/C Mice[a]

| Compound | Dose and Schedule | | % ILS | Survivors |
|---|---|---|---|---|
| cis-Dichlorodiammine- | 5 | mg/kg × 1 | 146 | 2/3 |
| platinum (II) | 8 | mg/kg × 1 | 62 | 0/2 |
| | 16 | mg/kg × 1 | −15 | 0/3 |
| uracil Class IA | 50 | mg/kg qid × 5 | 200 | 3/3 |
| | 100 | mg/kg qid × 5 | 166 | 2/3 |
| | 25 | mg/kg qid × 5 | 85 | 1/3 |
| | 125 | mg/kg × 1 | 107 | 1/3 |
| | 61.25 | mg/kg q3 hr × 5 | 137 | 1/3 |
| | 30.63 | mg/kg q3 hr × 8 | 37 | 0/3 |
| | 250 | mg/kg × 1 | −10 | 0/3 |
| | 500 | mg/kg × 1 | −60 | 0/3 |
| thymine Class IA | 100 | mg/kg qid × 5 | 124 | 1/3 |
| | 30.63 | mg/kg q3 hr × 7 | 156 | 2/3 |
| | 61.25 | mg/kg q3 hr × 7 | 103 | 1/3 |
| 5,6-dihydrothymine | 50 | mg/kg qid × 5 | 157 | 2/3 |
| Class IA | 100 | mg/kg qid × 5 | 0 | 0/3 |
| | 30.63 | mg/kg q3 hr × 8 | 75 | 1/3 |
| | 61.25 | mg/kg q3 hr × 6 | 121 | 2/3 |
| 1-methyluracil | 50 | mg/kg qid × 5 | 88 | 1/3 |
| Class IA | 100 | mg/kg qid × 5 | 19 | 0/3 |
| | 30.63 | mg/kg q3 hr × 8 | 34 | 0/3 |
| | 61.25 | mg/kg q3 hr × 8 | 110 | 1/3 |

[a]All experiments were terminated arbitrarily at 200% ILS and survivors tabulated at that time. All therapy was started on third day after tumor transplant. Untreated tumor controls died 10-11 days after transplant. In some instances, efforts to reproduce above results have shown considerable variability.

TABLE 6

Effects of cis-Dichlorodiammineplatinum (II) and 'Platinum-Uracil Blue' on Survival Times of Mice Bearing the Ehrlich Ascites Tumor[a]

| Compound | Dose (mg/kg) | Mean Survival Time days (+ S.D.) | % Increase in Mean Survival Time |
|---|---|---|---|
| Control | — | 8.3 ± 1.8 | — |
| cis-Dichlorodiam- mineplatinum (II) | 7 | 33.8 ± 16.9 | 307[b] |
| uracil Class IA | 100 | 24.7 ± 7.6 | 198 |
| uracil Class IA | 200 | 25.2 ± 7.4 | 204 |
| uracil Class IA | 300 | 36.0 ± 14.2 | 334 |
| Control | | 10.1 ± 2.8 | — |
| cis-Dichlorodiam- mineplatinum (II) | 7 | 29.7 ± 4.2 | 194 |
| uracil Class IA | 200 | 25.7 ± 4.5 | 154 |
| uracil Class IA | 300 | 30.3 ± 6.3 | 200 |
| uracil Class IA | 400 | 28.5 ± 4.2 | 182 |

[a]6 mice/group; each mouse received $10^7$ ascites tumor cells on day 0; treatment was as a single i. p. injection on day 3.
[b]2 animals in this group survived > 60 days.

TABLE 7

Effects of cis-Dichlorodiammineplatinum (II) and "Platinum Blues" on the ADJ/PC6A Tumor in Female, C− Mice[a]

| Compound | LD50 | ID 90 (90% Inhibition) | Therapeutic Index |
|---|---|---|---|
| cis-dichlorodiammine- platinum (II) | 13 mg/kg | 1.6 mg/kg | 8.1 |
| uracil Class IA[b] | 225 mg/kg | 94 mg/kg | 2.4 |
| 5,6-dihydrothymine Class IA | 135 mg/kg | 25 mg/kg | 5.4 |
| 6-chlorouracil Class IA | 200 mg/kg | 190 mg/kg | 1.05 |
| 5-carbethoxyuracil Class IA | 670 mg/kg | 250 mg/kg | 2.7 |
| 1-methyluracil Class IA | 670 mg/kg | 50 mg/kg | 13.4 |
| 5-hydroxymethyluracil Class IA | 40 mg/kg | 42 mg/kg | 0.95 |

[a]Injections, i.p. started 24 days after tumor implant, as single doses.
[b]Injections, i.p. started 24 days after tumor implant, given daily for 5 days.

Renal toxicity is the dose limiting side effect in higher animals and man under treatment with cis-dichlorodiammineplatinum(II). It is desirable to find other platinum drugs which cause much less severe renal toxicity. Described here are the results of histopathological examinations indicating that the "Platinum-Uracil Blue", Class IA, causes far less impairment of the kidneys than does cis-dichlorodiammineplatinum(II) or cis-dichloro(bis) cyclopantylamineplatinum(II), at roughly comparable therapeutic levels.

The protocols for these tests were as follows: Each group contained six female Swiss White mice; the tumored animals were given a transplant of a solid Sarcoma-180 tumor on day 0 and treatment was initiated on day 1; the animals were sacrificed on day 10 and the kidneys removed and prepared for histological evaluation; control groups were non-tumored, non-treated animals, and tumored, non-treated animals. Multiple sections of each kidney were examined. Since cis-dichloro(bis)cyclopentylamineplatinum(II) is a very insoluble compound, and usually tested as a slurry in arachis oil, we felt it necessary to test it as saturated solutions in saline in order to be comparable with the other drugs. The saturation concentration cannot be specified other than an estimate of less than 1 mg/100 ml. A very brief summary of the results are compiled in Table 8. The histopathologic degenerative changes are dose dependent in all cases. While the higher dose levels of cis-dichlorodiammineplatinum (II) and cis-dichloro(bis)cyclopentylamineplatinum (II) caused generalized vacuolar (hydropic) degeneration of the proximal convoluted tubules, the higher doses of the "Platinum-Uracil Blue" Class IA, produced mild degenerative changes generally, with some severe, multiple small foci of necrosis.

Since the function of a kidney containing foci of degenerative tissue should be less seriously impaired than kidneys in which entire anatomic/physiologic areas (i.e., proximal convoluted tubules) are involved, it is judged that the "Platinum-Uracil Blue" Class IA, is less nephrotoxic, (based upon renal histopathologic evidence) than the other two complexes, when compared at roughly equivalent therapeutic doses.

TABLE 8

Observed Renal Histopathological Changes in Mice Kidneys
[Limited to the proximal convoluted tubules]

1. cis-dichlorodiammineplatinum (II)

| Number of injections and time sequences between doses | Dosage Rate (mg/kg) | | | | |
|---|---|---|---|---|---|
| | 0.5 | 1.0 | 2.0 | 3.0 | 7.0 |
| 8 (every 3 hours) | normal | normal | — | — | — |
| 7 (every 24 hours) | — | normal | mild degenerative changes (cloudy swelling) | mild degenerative changes (cloudy swelling) | — |
| 1 [tumored animal] | — | — | — | — | extensive degenerative changes (hydropic degeneration) |
| 1 [non-tumored animal] | — | — | — | — | extensive degenerative changes (hydropic degeneration) |

2. uracil Class IA

| Number of injections and time sequence between doses | Dosage Rate (mg/kg) | | | |
|---|---|---|---|---|
| | 50 | 100 | 150 | 400 |
| 6 (every 3 hours) | — | — | focal areas of degeneration and necrosis. Hyaline casts also present. | — |
| 8 (every 3 hours) | — | focal areas of degeneration and necrosic. Hyaline casts also present. | — | — |
| 7 (every 24 hours) | mild congestion of renal cortex, otherwise normal. | extensive focal areas of degenerative change (hydropic degeneration) | isolated focal areas of degenerative change (hydropic generation) | — |
| 1 | — | — | — | mild degenerative changes (cloudy swelling) cortical hyperemia |

3. cis-dichloro(bis-cyclopentylamine)platinum (II)

| Number of injections and time sequence between doses | Dosage Rate (mg/kg) Saturated Solution |
|---|---|
| 10 (every 3 hours) | normal |
| 13 (every 3 hours) | normal |
| 16 (every 3 hours) | Mild to moderate degenerative changes. Hydropic degeneration. |
| 20 (every 3 hours) | Moderate generalized degenerative changes. Hydropic degeneration. |
| 7 (every 24 hours) | Mild generalized degenerative changes. Cloudy swelling. |

The following procedure was utilized to test the antimicrobal activity of the platinum complexes. The tests were performed with Escherichia coli-wild type, growing in test tube cultures. Using standardized techniques, growth in the medium was examined after the incorporation of the various test chemicals, using the increase in the optical density of the medium as against time. The bacteria were also periodically examined under a phase contrast microscope for evidence of elongation (filmentation). The results of the tests are set forth in Table 9.

TABLE 9

Summary of Bacterial Studies with "Platinum-Uracil Blues"

| Compound | ppm | 9:30 a.m. | 10:45 a.m. | 11:45 a.m. microscopic | 12:45 p.m. microscopic | 1:45 p.m. microscopic | 2:45 p.m. microscopic |
|---|---|---|---|---|---|---|---|
| Control | 0 | .19 | .32 | .46 normal | .62 normal | .85 normal | .95 normal |
| cis-Pt(NH$_3$)$_2$Cl$_2$ | 7 | .19 | .31 | .44 2× 50% | .62 2-4× 20% | .74 2-6× 40% | .78 2-6× 20% |
| cis-diaquodiammine-Pt(II)-6-methyluracil (prepared as in Ex. 1) | 5 | .16 | .30 | .43 normal | .54 normal | .77 normal | .90 normal |
| | 10 | .18 | .32 | .45 normal | .72 normal | .90 normal | 1.00 normal |
| | 20 | .18 | .32 | .45 normal | .74 normal | .96 normal | 1.00 normal |
| | 40 | .17 | .31 | .42 normal | .68 < normal | .90 normal | .90 normal |
| cis-diaquodiammine-Pt(II)-uracil (Ex. 1) | 5 | .19 | .25 | .39 clumping | .64 clumping | .80 some clumping | .90 some clumping |
| | 10 | .21 | .28 | 41 clumping | .68 clumping | .85 clumping | 1.00 clumping |
| | 20 | .23 | .29 | 40 clumping | .68 clumping | .90 clumping | .97 clumping |

TABLE 9-continued

Summary of Bacterial Studies with "Platinum-Uracil Blues"

| Compound | ppm | 40<br>9:30 a.m. | .25<br>11:00 a.m. | .30<br>12:00 p.m.<br>microscopic | 42 clumping<br>1:00 p.m.<br>microscopic | .53 clumping<br>2:00 p.m. | .72 extreme<br>clumping<br>3:20 p.m.<br>microscopic | .75 extreme<br>clumping |
|---|---|---|---|---|---|---|---|---|
| Control | 0 | .14 | .29 | .49 normal | .75 normal | .94 | .95 normal | |
| cis-Pt(NH$_3$)$_2$Cl$_2$ | 10 | .12 | .26 | .37 2–4× 60% | .49 2–8× 60% | .55 | .60 1–10× 90% | |
| cis-diaquodiammine-Pt(II)- | 5 | .13 | .24 | .44 normal | .73 normal | 1.00 | 1.00 normal | |
| 5,6-dihydrouracil | 10 | .13 | .23 | .39 clumping | .72 clumping | .95 | .95 normal | |
| (prepared as in Ex. 1) | 20 | .15 | .26 | .43 extreme clumping | .69 clumping | .81 | 1.00 some clumping | |
| | 40 | .18 | .27 | .40 extreme clumping | .66 clumping | .82 | 1.00 some clumping | |
| "Platinum-Acetamide Blue" | 5 | .19 | .32 | .48 normal | .78 normal | 1.00 | 1.00 normal | |
| | 10 | .27 | .32 | .32 normal | .32< normal | .32 | .31 < normal | |
| | 20 | .33 | .43 | .41 tiny cells | .41 tiny cells | .41 | .41 tiny cells | |
| | 40 | .64 | .95 | .95 tiny cells | .81 tiny cells | .85 | .85 tiny cells | |

The platinum complexes of the invention cause a clumping of the bacteria at fairly low concentrations. For example, the platinum-uracil complex causes clumping at levels of 5 ppm. Higher concentrations increase the clumping and result in eventual killing of the bacteria. The results would appear to indicate that the platinum complexes of the invention are potent anti-bacterial agents at low concentrations on the order of about 40 ppm.

The anti-viral activity of the platinum complexes of the invention was tested according to the following system. The system utilizes the Fowl Pox Virus and the embryonated egg. In the first type, a known viral concentration is incubated with a known amount of a drug to be tested for various periods of time. The innoculum is then injected into the embryonated egg and on approximately day 10, the egg is opened, the chorioallantoic membrane removed and the number of pock lesions counted. This type of test measures the in vitro inactivation of the Fowl Pox Virus by direct interaction with the new drug in a test tube. The second type of tests involves the innoculation of the embryonated egg with a known titer of Fowl Pox Virus. At various times thereafter, a single dose of the compound to be tested is injected onto the chorioallantoic membrane. Since after a period of a few hours the viral particles have disappeared and gone into the "eclipse phase" wherein the virion has been incorporated into the cell and begun its replication cycle, this test demonstrates the ability of the compound tested to enter into the cell and to disrupt the viral multiplication process. The results of these two types of tests are set forth in Tables 10 and 11.

TABLE 10

In Vitro Viral Inactivation of Fowl Pox Virus
with Platinum-Uracil[x] Complex
(6 × 10$^2$ μmg/ml of Pt.Uracil in incubation mixture)

| Length of incubation (hrs.) prior to incubation of mixture into embryonating eggs. | Average number of pock lesions counted per egg | % Reduction[1] |
|---|---|---|
| 0 Virus-Pt. | 0 | 100% |
| Virus-H$_2$O | 7.5 | |
| 1/6 Virus-Pt. | 0.3 | 96.2% |
| Virus-H$_2$O | 8.0 | |
| ½ Virus-Pt. | 0.5 | 92.6% |
| Virus-H$_2$O | 6.8 | |
| 1 Virus-Pt. | 0 | 100% |
| Virus-H$_2$O | 5.4 | |
| 2 Virus-Pt. | 0.6 | 90.9% |
| Virus-H$_2$O | 6.6 | |
| 4 Virus-Pt. | 0.25 | 94.7% |
| Virus-H$_2$0 | 4.75 | |
| 6 Virus-Pt. | 0.3 | 94.3% |

TABLE 10-continued

In Vitro Viral Inactivation of Fowl Pox Virus
with Platinum-Uracil[x] Complex
(6 × 10$^2$ μmg/ml of Pt.Uracil in incubation mixture)

| Length of incubation (hrs.) prior to incubation of mixture into embryonating eggs. | Average number of pock lesions counted per egg | % Reduction[1] |
|---|---|---|
| Virus-H$_2$O | 5.2 | |
| 8 Virus-Pt. | 0 | 100% |
| Virus-H$_2$O | 8.0 | |
| 26 Virus-Pt. | 0 | 100% |
| Virus-H$_2$O | 4.6 | |

[1]Percent Reduction = (1-Pt Blue/H$_2$O) × 100
[x]cis-diaquodiammine Pt (II)-Uracil (Ex. 1)

TABLE 11

In Vivo Anti-Viral Activity of Platinum-Uracil[x]
Complex Against Fowl Pox Virus
(0.36 mg Pt. Complex/egg

| Elasped time (hrs.) between inoculation of FPV onto chorio-allantoic membrane, and subsequent treatment with either Pt-Uracil complex or sterile distilled H$_2$O | Average number of pock lesions counted per egg. | % Reduction |
|---|---|---|
| 0 Virus-Pt. | 0 | 100% |
| Virus-H$_2$O | 6.75 | |
| 1/6 Virus-Pt. | 1.25 | 78.3% |
| Virus-H$_2$O | 5.75 | |
| ½ Virus-Pt. | 1.0 | 76.8% |
| Virus-H$_2$O | 4.3 | |
| 1 Virus-Pt. | 0 | 100% |
| Virus-H$_2$O | 7.5 | |
| 2 Virus-Pt. | 0.4 | 99.9% |
| Virus-H$_2$O | 6.8 | |
| 4 Virus-Pt. | 1.6 | 79.5% |
| Virus-H$_2$O | 7.8 | |

[x]cis-diaquodiammine Pt (II)-Uracil (Ex. 1)

For the tube inactivation tests, it was found that the virus is completely inactivated almost immediately upon exposure to the platinum-uracil complex. The inactivation of viable virions closely approaches 100%. This level remains at approximately 100% for up to 26 hours of incubation. This in vitro test demonstrates the extremely effective anti-viral activity of the platinum complexes of the invention.

In Table 12, the in vivo inactivation results indicate that up to four hours after the viral innoculation, the platinum-uracil complex is still inhibiting the number of pock lesions to provide a 68% reduction in the number of such lesions. A repetition of this test is given in Table 12.

TABLE 12

In Vivo Anti-Viral Activity of Platinum-Uracil[x] Complex Against Fowl Pox Virus (0.36 mg Pt. Blue/egg)

| Elapsed time (hrs.) between inoculation of FPV onto chorio-allantoic membrane, and subsequent treatment with either Pt-Uracil complex or sterile distilled H₂O. | Average number of pock lesions counted per egg. | % Reduction |
|---|---|---|
| 0 Virus-Pt | 0.6 | 91.1 |
| Virus-H₂O | 6.8 | |
| 1/6 Virus-Pt | 0.7 | 90.4 |
| Virus-H₂O | 7.0 | |
| ½ Virus-Pt | 1.0 | 88.1 |
| Virus-H₂O | 8.4 | |
| 1 Virus-Pt | 1.6 | 82.6 |
| Virus-H₂O | 9.2 | |
| 2 Virus-Pt | 2.5 | 69.5 |
| Virus-H₂O | 8.2 | |
| 4 Virus-Pt | 3.25 | 68.3 |
| Virus-H₂O | 10.25 | |

[x]Cis-diaquodiammine Pt (II)-Uracil (Ex. 1)

Again, after four hours, approximately 80% reduction in the number of pock lesions is apparent after innoculation of the virus.

We claim:

1. The blue or green platinum-[2,4-dioxopyrimidine] complex or the mixture thereof prepared by reacting a 2,4-dioxopyrimidine having the formula:

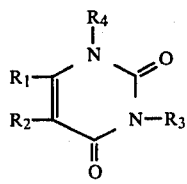

wherein
  $R_1$ and $R_2$ may be the same or different and are selected from the group consisting of H, lower alkyl, di-lower alkyl amino, di-halo lower alkyl amino, halogen, hydroxy, hydroxy lower alkyl, carboloweralkoxy,
  $R_3$ and $R_4$ may be the same or different and are selected from the group consisting of H, lower alkyl ribosyl, deoxyribosyl, ribosyl, triacetyl-, tribenzoyl- or 2',3' loweralkylidene ribosyl, ribosyl phosphates and deoxyribosyl phosphates or
  a 5,6-2H derivative thereof
  with cis-diaquodiammineplatinum(II) wherein the molar ratio of 2,4-dioxopyrimidine to cis-diaquodiammineplatinum(II) is from about 2:1 to about 1:1 at a temperature of from about 0° to about 55° C., a pH of from about 3 to about 8 and for a time sufficient to form said complex or mixture.

2. A complex according to claim 1 wherein $R_1$, $R_2$, $R_3$ and $R_4$ are each H.

3. A method of preparing a blue or green platinum[2-4-dioxopyrimidine] complex or a mixture thereof consisting essentially of reacting a 2,4-dioxopyrimidine having the formula:

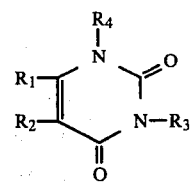

wherein
  $R_1$ and $R_2$ may be the same or different and are selected from the group consisting of H, lower alkyl, di-lower alkyl amino, di-halo lower alkyl amino, halogen, hydroxy, hydroxy lower alkyl, carboloweralkoxy
  $R_3$ and $R_4$ may be the same or different and are selected from the group consisting of H, lower alkyl ribosyl, deoxyribosyl, triacetyl-, tribenzoyl- or 2',3'-loweralkylidene ribosyl, ribosyl phosphates and deoxyribosyl phosphates or
  a 5,6-2H derivative thereof
  with cis-diaquodiammineplatinum(II) in aqueous solution wherein the molar ratio of 2,4-dioxopyrimidine to cis-diaquodiammineplatinum(II) is from about 2:1 to about 1:1 at a temperature of from about 0 to about 55° C., at a pH of from about 3 to about 8 and for a time sufficient to form said complex or mixture and isolating said complex or mixture.

4. A method according to claim 3 wherein said temperature is about room temperature.

5. A method according to claim 4 wherein said reaction is conducted for from about 1 to about 21 days.

6. The blue or green platinum complex or the mixture thereof prepared by reacting a 2,4-dioxopyrimidine having the structural formula:

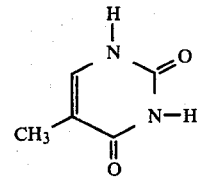

of the 5,6-2H derivative thereof with cis-diaquodiammineplatinum(II) wherein the molar ratio of 2,4-dioxopyrimidine to cis-diaquodiammineplatinum(II) is from about 2:1 to about 1:1 at a temperature of from about 0° to about 55° C., a pH of from about 3 to about 8 and for a time sufficient to form said complex or mixture.

7. A composition adapted for intraperitoneal, intramuscular, subcutaneous or intravenous injection or per os administration to treat malignant tumor cells sensitive to a complex of claim 1 comprising, in unit dosage form, a pharmaceutically acceptable carrier and from about 0.1 mg/ml to about 50 mg/ml of a complex of claim 1.

8. A method for the treatment of malignant tumor cells sensitive to a complex of claim 1 comprising the administration to a living being afflicted therewith from about 1 mg/kg to about 800 mg/kg of body weight of a complex according to claim 1.

* * * * *